United States Patent
Teng et al.

(10) Patent No.: US 10,688,010 B2
(45) Date of Patent: Jun. 23, 2020

(54) ADJUSTING ASSEMBLY AND EXOSKELETON ROBOT COMPRISING THE SAME

(71) Applicant: FREE BIONICS TAIWAN INC., Hsinchu (TW)

(72) Inventors: Ming-Chang Teng, Hsinchu (TW); Yi-Jeng Tsai, Taoyuan (TW)

(73) Assignee: FREE BIONICS TAIWAN INC., Hsinchu (TW)

( * ) Notice: Subject to any disclaimer, the term of this patent is extended or adjusted under 35 U.S.C. 154(b) by 415 days.

(21) Appl. No.: 15/860,194

(22) Filed: Jan. 2, 2018

(65) Prior Publication Data
US 2019/0201274 A1    Jul. 4, 2019

(51) Int. Cl.
*A61H 3/00* (2006.01)
*B25J 9/06* (2006.01)
(Continued)

(52) U.S. Cl.
CPC .............. *A61H 3/00* (2013.01); *B25J 9/0006* (2013.01); *B25J 18/02* (2013.01); *A61B 34/30* (2016.02);
(Continued)

(58) Field of Classification Search
CPC . A61F 2002/6854; B25J 18/02; B25J 9/0006; B25J 9/104; B25J 9/1694;
(Continued)

(56) References Cited

U.S. PATENT DOCUMENTS 8,070,700 B2    12/2011    Kazerooni et al.
9,687,409 B2    6/2017    Teng et al.
(Continued)

FOREIGN PATENT DOCUMENTS

CN        105105896        11/2016
EP        2923685 A1       9/2015
(Continued)

OTHER PUBLICATIONS

Search Report dated Feb. 1, 2019 by the European Patent Office for counterpart application 18178122.0.
(Continued)

*Primary Examiner* — Tu A Vo
(74) *Attorney, Agent, or Firm* — WPAT, P.C., Intellectual Property Attorneys; Anthony King

(57) ABSTRACT

An adjusting assembly for an exoskeleton robot. The adjusting assembly includes a first plate, a second plate pivotably connected to the first plate via a first shaft, and a second shaft. The first plate includes at least one pin aligned with each other in a first direction. The second shaft, extending in parallel with the first shaft in the first direction, includes a body and at least one recess. The second shaft is configured to rotate to a first position to accommodate the at least one pin in the at least one recess, and to a second position to release the at least one pin from the at least one recess. At the first position the second plate is blocked from rotation about the first shaft by the body. At the second position the second plate is allowed to rotate about the first shaft.

20 Claims, 10 Drawing Sheets

(51) Int. Cl.
    *B25J 9/00*       (2006.01)
    *B25J 18/02*     (2006.01)
    *A61B 34/30*    (2016.01)

(52) U.S. Cl.
    CPC .... *A61H 2003/007* (2013.01); *A61H 2205/10* (2013.01)

(58) Field of Classification Search
    CPC ..... Y10T 403/32336; Y10T 403/32319; Y10T 403/32327; Y10T 403/32344; Y10T 403/32352; Y10T 403/32361; Y10T 403/32368; Y10T 403/32377; Y10T 403/32385; Y10T 403/32393; Y10T 403/32401; Y10T 403/32409; A61B 34/30; A61H 2205/10; A61H 3/00; A61H 1/0244; A61H 1/0262; A61H 2001/0248; A61H 2001/0251; A61H 2003/007; A61H 2201/0192; A61H 2201/1215; A61H 2201/1223; A61H 2201/149; A61H 2201/163; A61H 2201/1642; A61H 2201/165; A61H 2201/1652; A61H 2201/5007; A61H 2201/5038; A61H 2201/5079; A61H 2201/5084; A61H 2201/5097; A61H 2205/088; A61H 2205/102; E05D 11/1007; E05D 11/10; E05D 11/1014; E05D 11/1021; E05D 11/1028; E05D 2011/1035

See application file for complete search history.

(56) References Cited

U.S. PATENT DOCUMENTS

| | | | | |
|---|---|---|---|---|
| 9,808,073 | B1* | 11/2017 | Maxwell | A61H 3/008 |
| 2014/0276261 | A1 | 9/2014 | Caires et al. | |
| 2016/0331625 | A1* | 11/2016 | Sankai | B25J 9/0006 |
| 2016/0374887 | A1* | 12/2016 | Wu | A61H 3/00 623/31 |
| 2018/0338883 | A1* | 11/2018 | Chavarria | A61H 1/0244 |
| 2019/0076284 | A1* | 3/2019 | Kwark | A61F 5/3753 |

FOREIGN PATENT DOCUMENTS

| | | |
|---|---|---|
| EP | 3103427 A1 | 12/2016 |
| GB | 1138890 A | 1/1969 |

OTHER PUBLICATIONS

U.S. Pat. No. 9,687,409 is the counterpart application to Foreign Patent Document EP2923685.

US Patent Publication 20160331625 is the counterpart application to Foreign Patent Document 3103427A1.

\* cited by examiner

ADJUSTING ASSEMBLY AND EXOSKELETON ROBOT COMPRISING THE SAME

BACKGROUND

An exoskeleton robot is a wearable mobile machine that supports the body of a user and move limbs of the user. One of the main applications is medical. An exoskeleton robot can help persons who lose or lose control of their legs or arms due to illness or accidental injury. While exoskeleton robots are helpful devices for physically challenged persons, it may be laborious for these persons to put on or take off an exoskeleton robot.

It may therefore be desirable to have an adjusting assembly to facilitate dressing or undressing an exoskeleton robot user.

The present invention is directed to an adjusting assembly for an exoskeleton robot, and an exoskeleton robot comprising the adjusting assembly.

Embodiments according to the present invention provide an adjusting assembly for an exoskeleton robot. The adjusting assembly includes a first plate, a second plate pivotably connected to the first plate via a first shaft, and a second shaft. The first plate includes at least one pin aligned with each other in a first direction. The second shaft, extending in parallel with the first shaft in the first direction, includes a body and at least one recess. The second shaft is configured to rotate to a first position to accommodate the at least one pin in the at least one recess, and to a second position to release the at least one pin from the at least one recess. At the first position the second plate is blocked from rotation about the first shaft by the body. At the second position the second plate is allowed to rotate about the first shaft.

In an embodiment, the first plate further includes a first block, and the at least one pin includes a first pair of pins on opposite surfaces of the first block.

In another embodiment, the first plate further includes a second block, and the at least one pin includes a second pair of pins on opposite surfaces of the second block.

In yet another embodiment, the second shaft further includes a first locking member, a second locking member and a third locking member between the first locking member and the second locking member. In addition, the first locking member, second locking member and third locking member are integral with the body.

In still another embodiment, the at least one recess further includes a first recess defined between the first locking member and the third locking member. The first recess is configured to accommodate one of the first pair of pins.

In yet still another embodiment, the at least one recess further includes a second recess defined between the second locking member and the third locking member. The second recess is configured to accommodate one of the second pair of pins.

In still yet another embodiment, the third locking member includes a first tab and a second tab, and the at least one recess further includes a third recess defined between the first tab and the second tab. The first recess, the second recess and the third recess are configured to communicate with each other in the first direction.

In a further embodiment, the third recess is configured to accommodate the other one of the first pair of pins and the other one of the second pair of pins.

In another further embodiment, the adjusting assembly further includes a lever connected to the first locking member of the second shaft. The lever is configured to cause the second shaft to rotate as the lever rotates.

In yet another further embodiment, the first plate is secured to a waist assembly of the exoskeleton robot, and the second plate is connected to a leg assembly of the exoskeleton robot.

Embodiments according to the present invention also provide an exoskeleton robot. The exoskeleton robot includes a waist assembly, a leg assembly and an adjusting assembly. The adjusting assembly includes a first plate, a second plate pivotably connected to the first plate via a first shaft, and a second shaft. The first plate includes at least one pin aligned with each other in a first direction. The second shaft, extending in parallel with the first shaft in the first direction, includes a body and at least one recess. The second shaft is configured to rotate to a first position to accommodate the at least one pin in the at least one recess, and to a second position to release the at least one pin from the at least one recess. At the first position the second plate is blocked from rotation about the first shaft by the body. At the second position the second plate is allowed to rotate about the first shaft.

The foregoing has outlined rather broadly the features and technical advantages of the present invention in order that the detailed description of the invention that follows may be better understood. Additional features and advantages of the invention will be described hereinafter, and form the subject of the claims of the invention. It should be appreciated by those skilled in the art that the conception and specific embodiment disclosed might be readily utilized as a basis for modifying or designing other structures or processes for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

Aspects of the present disclosure are best understood from the following detailed description when read with the accompanying figures. It is noted that, in accordance with the standard practice in the industry, various features are not drawn to scale. In fact, the dimensions of the various features may be arbitrarily increased or reduced for clarity of discussion.

The objectives and advantages of the present invention will become apparent upon reading the following description and upon reference to the accompanying drawings in which.

DESCRIPTION OF THE EMBODIMENTS

Embodiments of the present disclosure are discussed in detail below. It should be appreciated, however, that the present disclosure provides many applicable inventive concepts that can be embodied in a wide variety of specific contexts. The specific embodiments discussed are merely illustrative and do not limit the scope of the disclosure.

It shall be understood that, although the terms first, second, third, etc. may be used herein to describe various elements, components, regions, layers or sections, these elements, components, regions, layers or sections are not limited by these terms. Rather, these terms are merely used to distinguish one element, component, region, layer or section from another region, layer or section. Thus, a first element, component, region, layer or section discussed below could be termed a second element, component, region, layer or section without departing from the teachings of the present inventive concept.

The terminology used herein is for the purpose of describing particular example embodiments only and is not intended to be limited to the present inventive concept. As used herein, the singular forms "a," "an" and "the" are intended to include the plural forms as well, unless the context clearly indicates otherwise. It shall be further understood that the terms "comprises" and "comprising," when used in this specification, point out the presence of stated features, integers, steps, operations, elements, or components, but do not preclude the presence or addition of one or more other features, integers, steps, operations, elements, components, or groups thereof.

Further, spatially relative terms, such as "beneath," "below," "lower," "above," "upper", "lower", "left", "right" and the like, may be used herein for ease of description to describe one element or feature's relationship to another element(s) or feature(s) as illustrated in the figures. The spatially relative terms are intended to encompass different orientations of the device in use or operation in addition to the orientation depicted in the figures. The apparatus may be otherwise oriented (rotated 90 degrees or at other orientations) and the spatially relative descriptors used herein may likewise be interpreted accordingly. It will be understood that when an element is referred to as being "connected to" or "coupled to" another element, it may be directly connected to or coupled to the other element, or intervening elements may be present.

The embodiments of the present invention are shown in the following description with the drawings, wherein similar or same components are indicated by similar reference numbers.

Figure 1A:
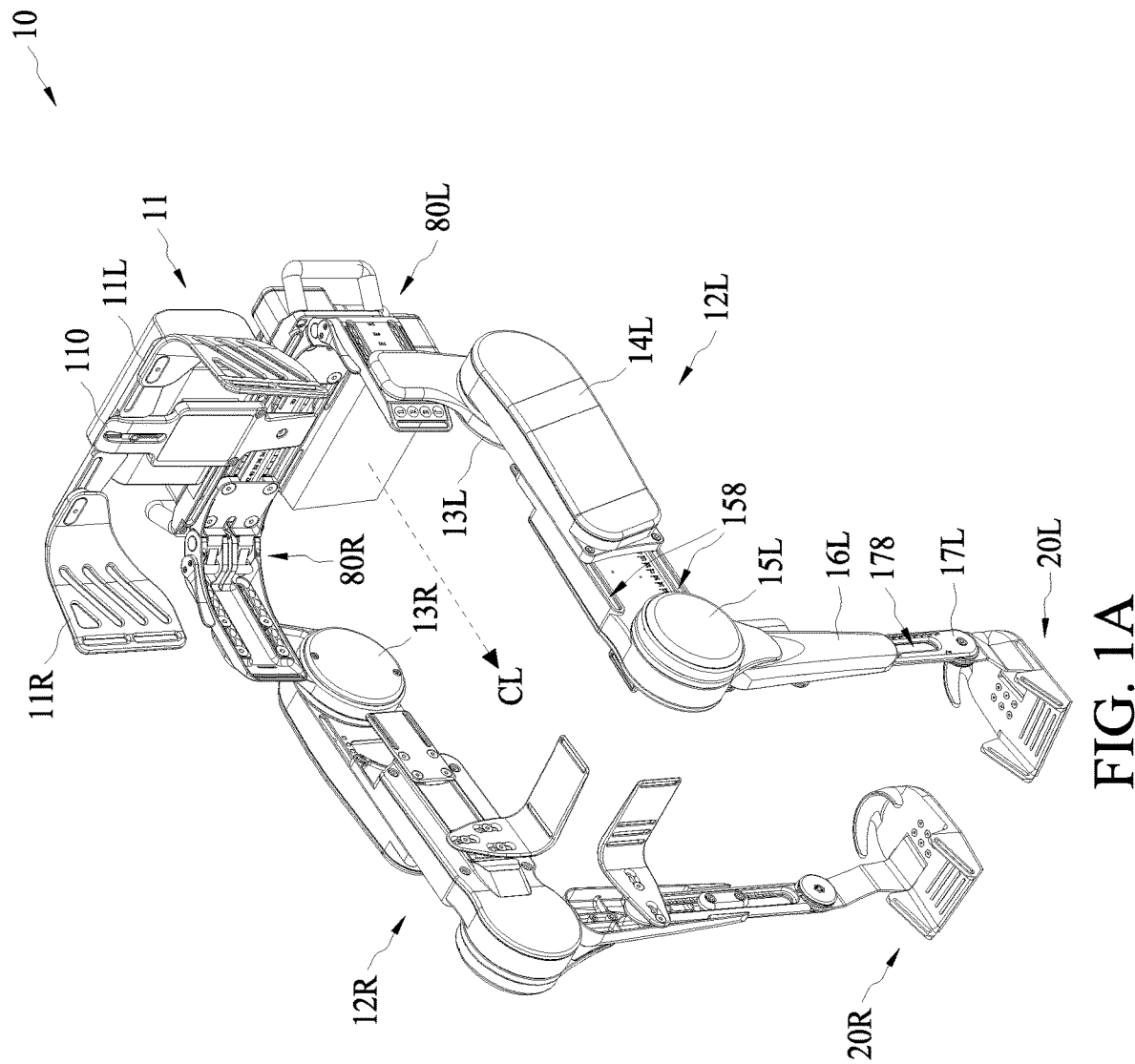
FIG. 1A is a perspective view of an exoskeleton robot in a sitting posture, in accordance with some embodiments of the present invention.

FIG. 1A is a perspective view of an exoskeleton robot 10 in a sitting posture, in accordance with some embodiments of the present invention.

Referring to FIG. 1A, the exoskeleton robot 10 includes a waist assembly 11, a right adjusting assembly 80R, a left adjusting assembly 80L, a right leg assembly 12R, a left leg assembly 12L, a right shoe assembly 20R and a left shoe assembly 20L.

The waist assembly 11 is configured to support a user of the exoskeleton robot 10 at the waist. Specifically, the waist assembly 11 includes a main plate 110, a right bracing member 11R and a left bracing member 11L. The main plate 110 extends vertically in a first direction so that the back of the user near the waist can lean against. In addition, the main plate 110, the right bracing member 11R and the left bracing member 11L together define a space for accommodating the chest of the user.

Figure 1B:
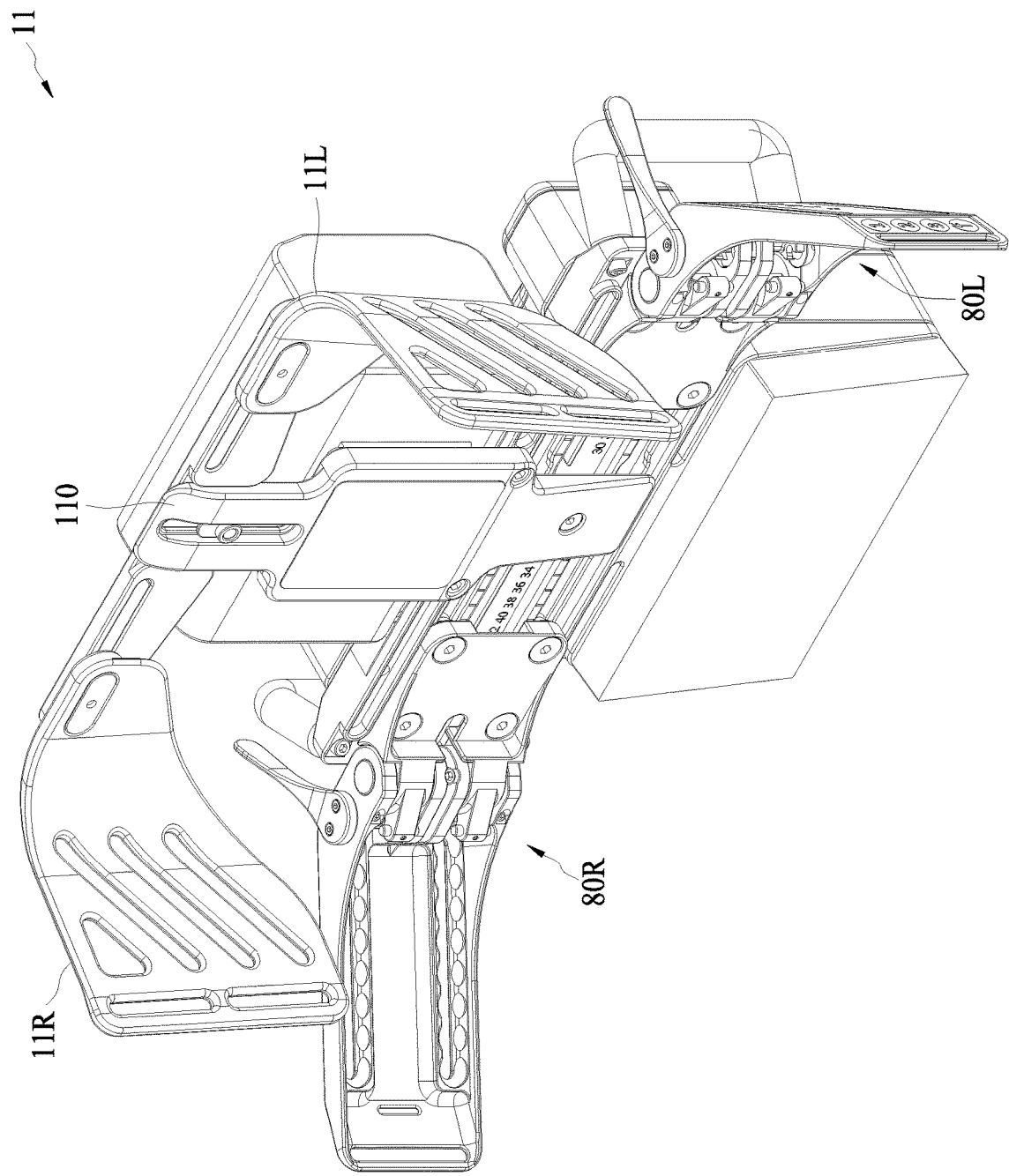
FIG. 1B is a perspective view of adjusting assemblies of the exoskeleton robot illustrated in FIG. 1A, in accordance with some embodiments of the present invention.

FIG. 1B is an amplified view of adjusting assemblies 80R and 80L of the exoskeleton robot 10 illustrated in FIG. 1A, in accordance with some embodiments of the present invention. Referring to FIG. 1B, the right adjusting assembly 80R and the left adjusting assembly 80L, arranged on the right side and the left side of the main plate 110 of the waist assembly 11, respectively, are coupled to the main plate 110. The right adjusting assembly 80R and the left adjusting assembly 80L are configured to facilitate a user to put on the exoskeleton robot 10. The structure and components of the right adjusting assembly 80R and the left adjusting assembly 80L will be discussed in detail by reference to FIG. 3. Moreover, functions of the right adjusting assembly 80R and the left adjusting assembly 80L will be discussed in detail by reference to FIGS. 4A, 5A and 6A.

In the present invention, the exoskeleton robot 10 includes several elements or components that appear in pairs. For example, the bracing members 11R and 11L are symmetric to each other with respect to the main plate 110 of the waist assembly 11. In addition, the leg assemblies 12R and 12L are symmetric to each other with respect to the main plate 110. Also, the right adjusting assembly 80R and the left adjusting assembly 80L are symmetric to each other with respect to the main plate 110. In the following description, only one of paired elements or components will be discussed in detail for brevity.

Referring back to FIG. 1A, the left leg assembly 12L is pivotably connected to the left adjusting assembly 80L via a left hip joint 13L. As a result, the left leg assembly 12L is rotatable with respect to the left adjusting assembly 80L. The left leg assembly 12L includes a thigh stand 14L, a shank stand 16L, a knee joint 15L and an ankle joint 17L in addition to the hip joint 13L. The thigh stand 14L, having an elongated shape, is pivotably connected at one side (not numbered) to the left adjusting assembly 80L via the hip joint 13L, and pivotably connected at another side (not numbered) to the shank stand 16L via the knee joint 15L. As a result, the thigh stand 14L and the shank stand 16L are rotatable with respect to the knee joint 15L. Moreover, the thigh stand 14 is movable along a first adjusting means 158 of the knee joint 15L in the elongated direction so that the length of the left leg assembly 12L at the thigh portion is adjustable to suit the user's need. In the present embodiment, the first adjusting means 158 includes a pair of slots stretched in the elongated direction. In other embodiments, the first adjusting means 158 may include grooves, rails or sliding rods that facilitate the adjustment lengthwise.

The shank stand 16L, also having an elongated shape, is pivotably connected at one side (not numbered) to the thigh stand 14L via the knee joint 15L, and pivotably connected at another side (not numbered) to the left shoe assembly 20L via the ankle joint 17L. As a result, the shank stand 16L and the left shoe assembly 20L are rotatable with respect to the ankle joint 17L. Moreover, the shank stand 14L is movable along a second adjusting means 178 of the ankle joint 17L in the elongated direction of the shank stand 14L so that the length of the left leg assembly 12L at the shank portion is adjustable to suit the user's need. In the present embodiment, the second adjusting means 178 includes a slot stretched in the elongated direction of the shank stand 14L. Alternatively, the second adjusting means 178 may include grooves, rails or sliding rods that facilitate the adjustment lengthwise.

The thigh stand 14L, shank stand 16L, hip joint 13L, knee joint 15L and ankle joint 17L are similar to those disclosed in the U.S. application Ser. No. 14/519,145 (herein after the '145 application), entitled "Walking Assist Device," filed 21 Oct. 2014 by the same inventors of the subject application, and therefor are not described in detail. For more information on the physical relationship among and the functions of the thigh stand 14L, shank stand 16L, hip joint 13L, knee joint 15L and ankle joint 17L, reference can be made to the disclosure of the '145 application.

Figure 2:
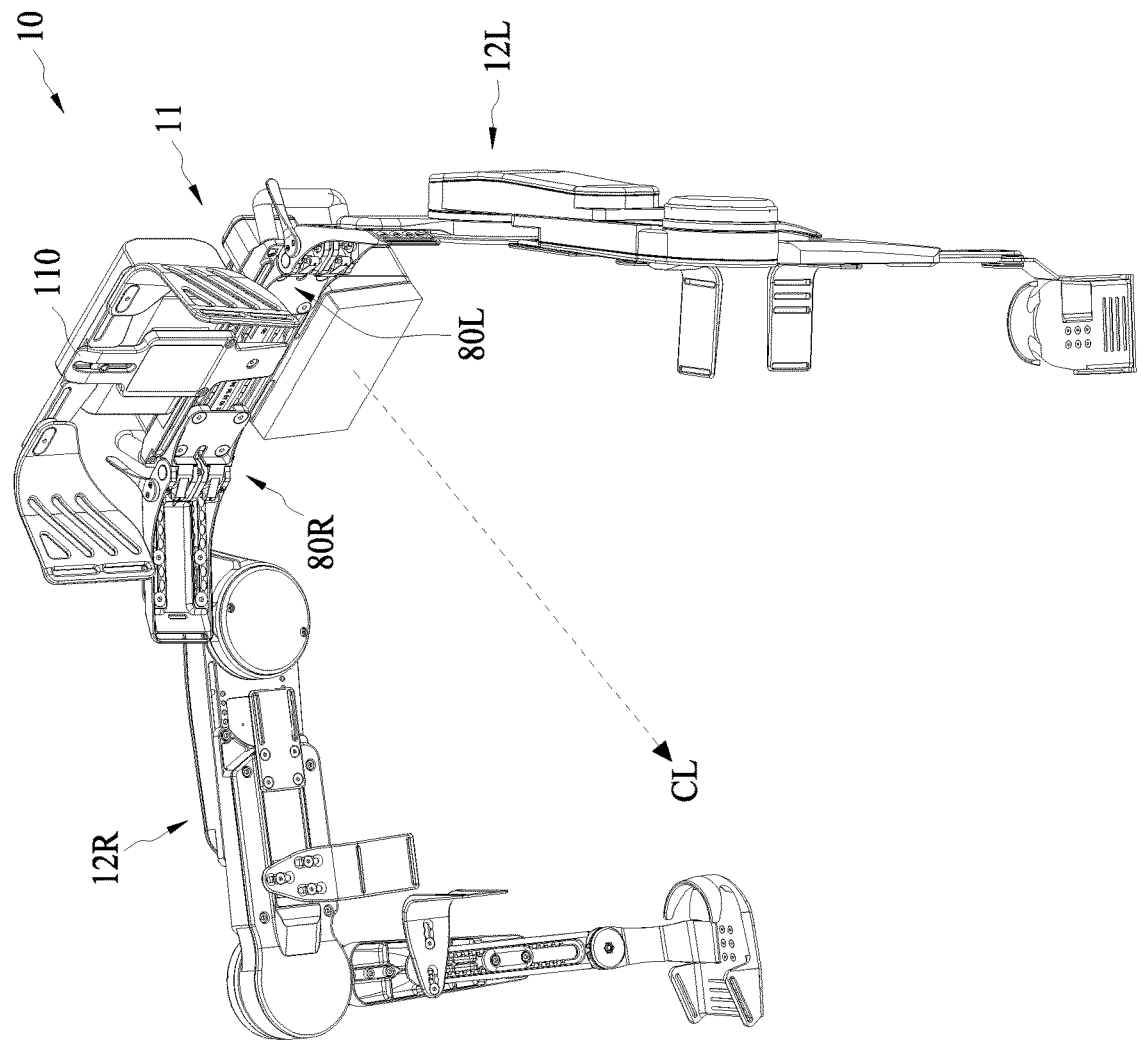
FIG. 2 is an amplified view of the exoskeleton robot illustrated in FIG. 1A with its leg assemblies in an unfolded position.

FIG. 2 is a perspective view of the exoskeleton robot 10 illustrated in FIG. 1A with its leg assemblies 12R and 12L in an unfolded position.

Each of the right adjusting assembly 80R and the left adjusting assembly 80L operates in either a locked state or an unlocked state. When the right adjusting assembly 80R is in the locked state, the right leg assembly 12R associated with the right adjusting assembly 80R is held in a folded position. Similarly, when the left adjusting assembly 80L is in the locked state, the left leg assembly 12L associated with the left adjusting assembly 80L is held in a folded position. Accordingly, when both the right adjusting assembly 80R and the left adjusting assembly 80L are in the locked state, the right leg assembly 12R and the left leg assembly 12L are held close to each other as shown in FIG. 1A, and are disposed proximal to a central line CL that is normal to the main plate 110. The locked-state right adjusting assembly 80R and left adjusting assembly 80L ensure a user to be well cladded in the exoskeleton robot 10 and to safely operate the exoskeleton robot 10.

In contrast, when the right adjusting assembly 80R is in the unlocked state, the right leg assembly 12R associated with the right adjusting assembly 80R can be released from the folded position and enters into an unfolded position. Similarly, when the left adjusting assembly 80L is in the unlocked state, the left leg assembly 12L associated with the left adjusting assembly 80L can be released from the folded position and enters into an unfolded position. Accordingly, when both the right adjusting assembly 80R and the left adjusting assembly 80L are in the unlocked state, the right leg assembly 12R and the left leg assembly 12L can be separated from each other as shown in FIG. 2, and are disposed remote to the central line CL.

Referring to FIG. 2, the unlocked-state right adjusting assembly 80R and left adjusting assembly 80L create a wide open space that facilitates a user to put on or take off the exoskeleton robot 10. Specifically, users of the exoskeleton robot 10 are generally physically challenged with limited mobility, and a majority of them may use wheel chairs. In some existing approaches, to put on an exoskeleton robot, a user may be lifted from a wheel chair by other and then "loaded" to the exoskeleton robot, which is relatively inconvenient. In contrast, with the right adjusting assembly 80R and left adjusting assembly 80L in an unlocked state, an open space is provided, which facilitates an easy access to a wheel-chair user and hence dressing or undressing the user of the exoskeleton robot 10.

Figure 3:
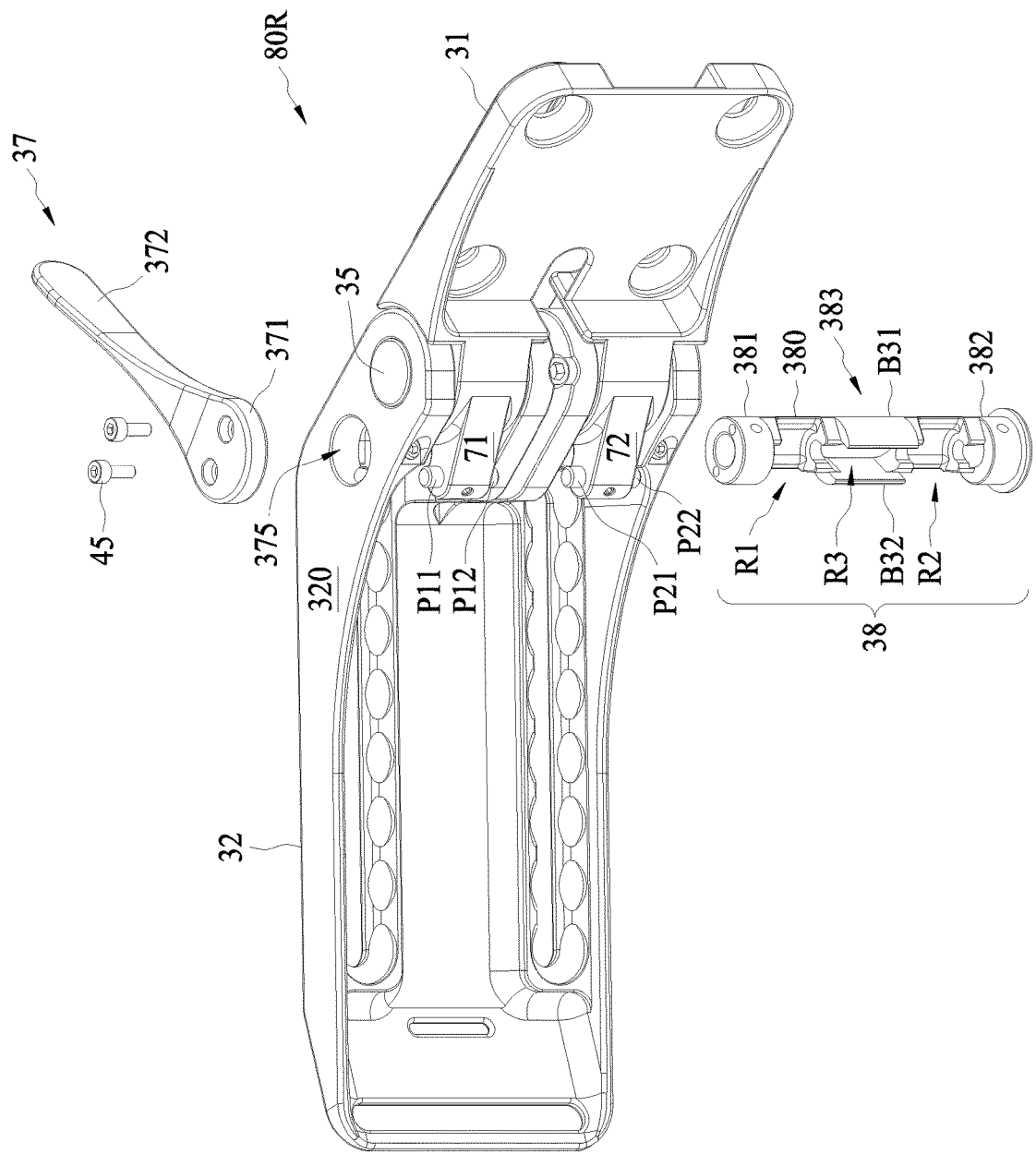
FIG. 3 is an exploded view of a right adjusting assembly illustrated in FIG. 1B.

FIG. 3 is an exploded view of the right adjusting assembly 80R illustrated in FIG. 1B.

Referring to FIG. 3, the right adjusting assembly 80R includes a first plate 31, a second plate 32, a first shaft 35, a lever 37 and a second shaft 38.

The first plate 31 is secured to the waist assembly 11, and thus is kept immobile with respect to the waist assembly 11 either in a locked state or unlocked state of the right adjusting assembly 80R. In the present embodiment, the first plate 31 is secured to the main plate 110 of the waist assembly 11. The first plate 31 extends in a second direction substantially orthogonal to the first direction in which the main plate 110 extends.

The second plate 32 is pivotably connected to the first plate 31 via the first shaft 35. In a locked state of the right adjusting assembly 80R, as shown in FIG. 1A, the second plate 32 extends in parallel with the central line CL in a third direction substantially orthogonal to the first direction and the second direction. In an unlocked state, the second plate 32 is allowed to rotate, outwardly from the locked position, about the first shaft 35 with respect to the first plate 31.

The lever 37 includes an engaging head 371 and a handle 372. The engaging head 371 is configured to engage the second shaft 38 at an opening 370 on a surface 320 of the second plate 32 by fastening means 45. As a result, the second shaft 38 rotates as the lever 37 rotates in response to a force exerted at the handle 372.

The second shaft 38, substantially in the form of a cylinder, includes a body 380, a first locking member 381, a second locking member 382 and a third locking member 383 between the first locking member 381 and the second locking member 382.

The body 380 extends in the first direction and is integral with the first locking member 381, the second locking member 382 and the third locking member 383. The body 380 functions to block the second plate 32 from rotation about the first shaft 35 when the second plate 32 is held in a locked state, which will be discussed in detail by reference to FIGS. 4A and 4B.

In the present embodiment, the first locking member 381 takes the form of a cylinder and engages with the engaging head 371 of the lever 37. In addition, the second locking member 382 also takes the form of a cylinder.

The third locking member 383 may be equally spaced apart from the first locking member 381 and the second locking member 382. Accordingly, a first recess R1 is defined between the first locking member 381 and the third locking member 383. In addition, a second recess R2 is defined between the second locking member 382 and the third locking member 383.

The third locking member 383 includes a first tab B31 and a second tab B32. The first tab B31 and the second tab B32 extend in the first direction and together define a third recess R3 that communicates with the first recess R1 and the second recess R2 in an axial direction (the first direction) of the second shaft 38.

The first plate includes a first block 71 and a second block 72. The first block 71 and the second block 72 are kept immobile as the second plate 32 rotates about the first shaft 35. At least one of the first block 71 and the second block 72 is provided with a pin to work in conjunction with the second shaft 38 so as to block the second plate 32 from rotation when the second plate 32 is held in a locked state. The pin may be formed integral with the at least one of the first block 71 and the second block 72. In the present embodiment, the first block 71 is provided with a first pair of pins P11 and P12 on opposite surfaces (not numbered) of the first block 71. In addition, the second block 72 is provided with a second pair of pins P21 and P22 on opposite surfaces (not numbered) of the second block 72. Further, these pins P11, P12, P21 and P22 align with each other in the first direction.

The first block 71 together with the first pair of pins P11, P12 is sized or shaped in the first direction so that a first pin P11 and a portion of the first block 71 where the first pin P11 is disposed are accommodated in the first recess R1, while a second pin P12 is accommodated in the third recess R3 of the second shaft 38, when the second plate 32 is held in a locked state. Similarly, the second block 72 together with the second pair of pins P21, P22 is sized or shaped in the first direction so that a third pin P22 and a portion of the second block 72 where the third pin is disposed are accommodated in the second recess R2 while a fourth pin. P21 is accommodated in the third recess R3 of the second shaft 38, when the second plate 32 is held in a locked state. Functions of the first plate 31, second plate 32 and the second shaft 38 are discussed in detail by reference to the operations in FIGS. 4A, 5A and 6A below, FIG. 4A is a perspective view of the right adjusting assembly 80R illustrated in FIG. 1B in a locked state, in accordance with some embodiments of the present invention.

Figure 4A:
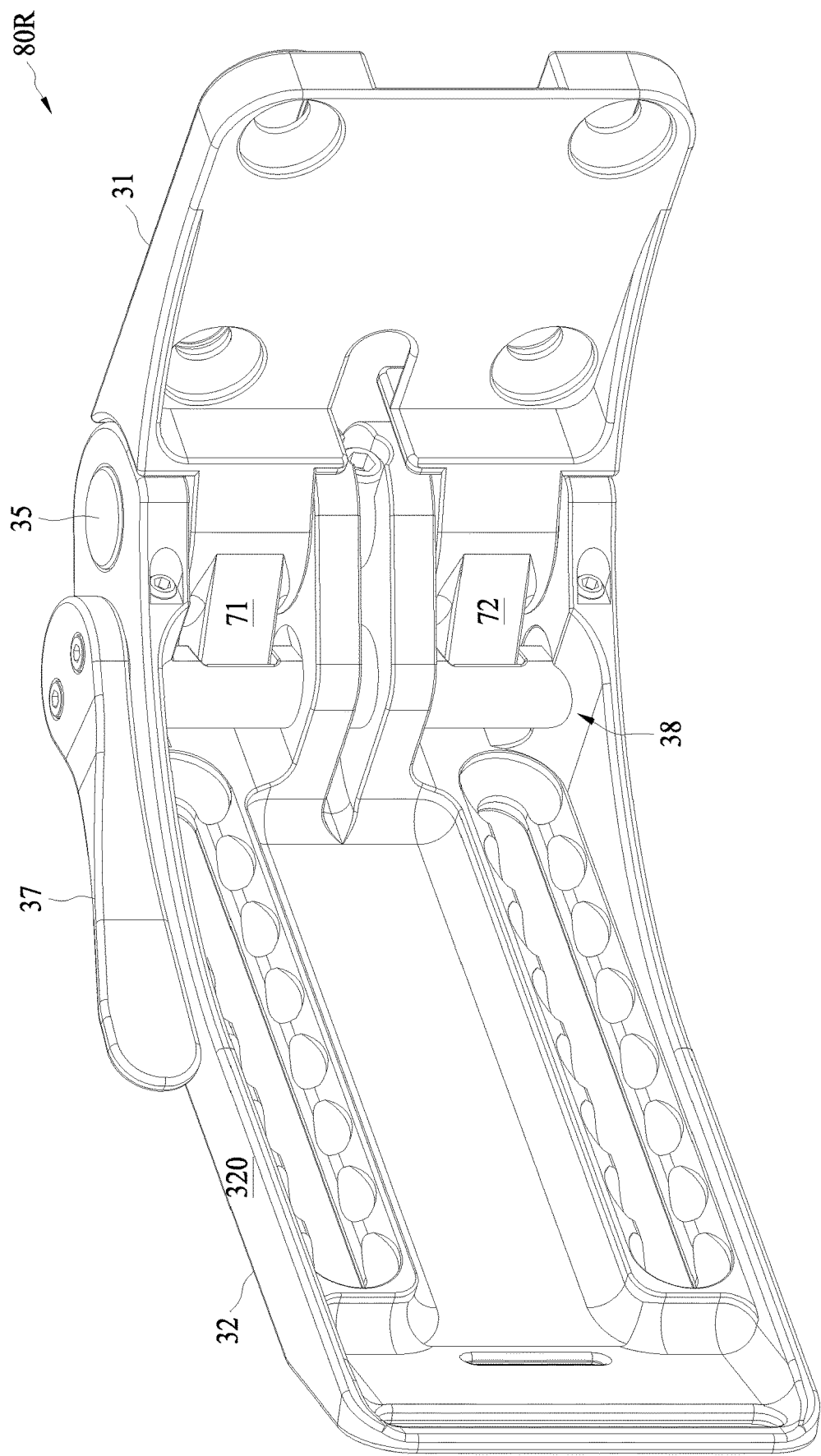
FIG. 4A is a perspective view of the right adjusting assembly illustrated in FIG. 1B in a locked state, in accordance with some embodiments of the present invention.

Referring to FIG. 4A, during a locked state, the pins P11 and P12 associated with the first block 71 are accommodated in the first recess R1 and the third recess R3 of the second shaft 38, respectively, while the pins P22 and P21 associated with the second block 72 are accommodated in the second recess R1 and the third recess R3 of the second shaft 38, respectively. These pins P11, P12, P21 and P22 are enclosed in the second shaft 38 and hidden from the current view of FIG. 4A.

Figure 4B:
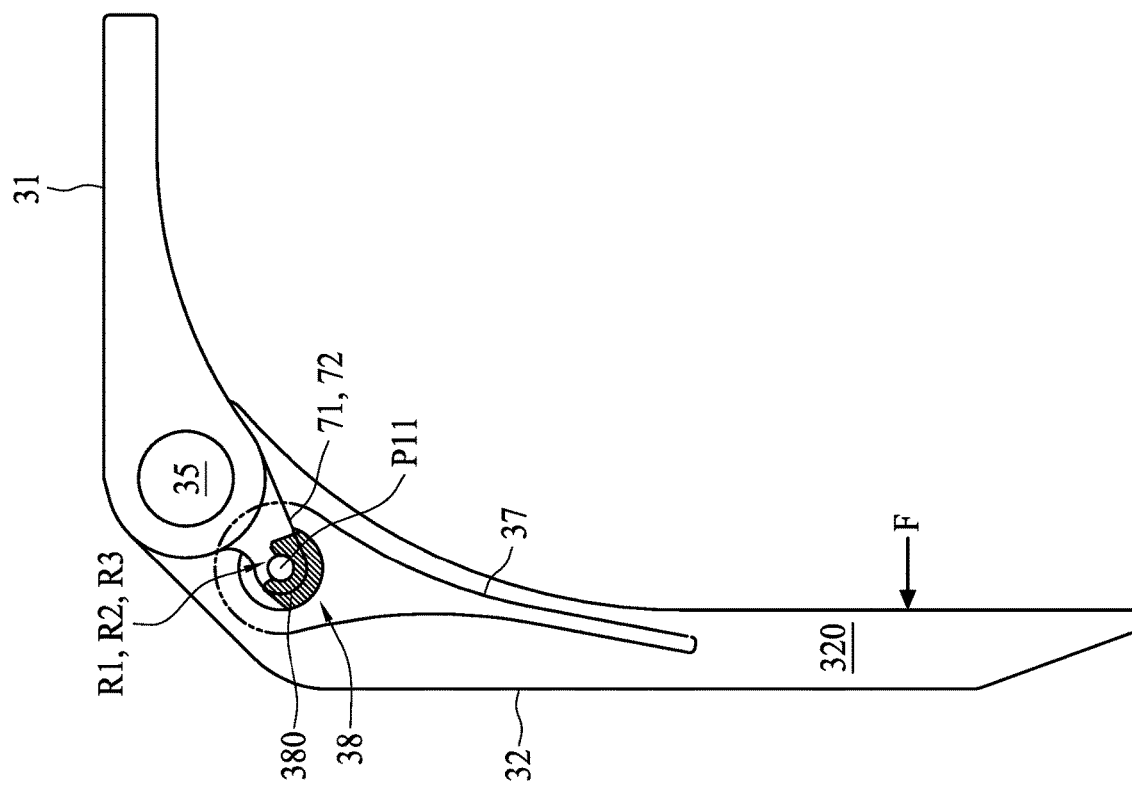
FIG. 4B is a schematic top view of the right adjusting assembly illustrated in FIG. 4A.

FIG. 4B is a schematic top view of the right adjusting assembly 80R illustrated in FIG. 4A.

Referring to FIG. 4B, when the second shaft 38 is rotated by the lever 37 to a first position, the pins P11, P12, P21 and P22 are enclosed in the second shaft 38. Meanwhile, the body 380 comes into contact with the first block 71 and the second block 72. Consequently, when an external force F is exerted in an attempt to move the second plate 32 away from the central line CL, the body 380 presses against the first block 71 and the second block 72 and thus blocks an outward rotation of the second plate 32 about the first shaft 35. As a result, during the locked state, the right leg assembly 12R coupled to the second plate 32 is not allowed to move outwardly with respect to the central line Cl and thus is held in a folded position.

Figure 5A:
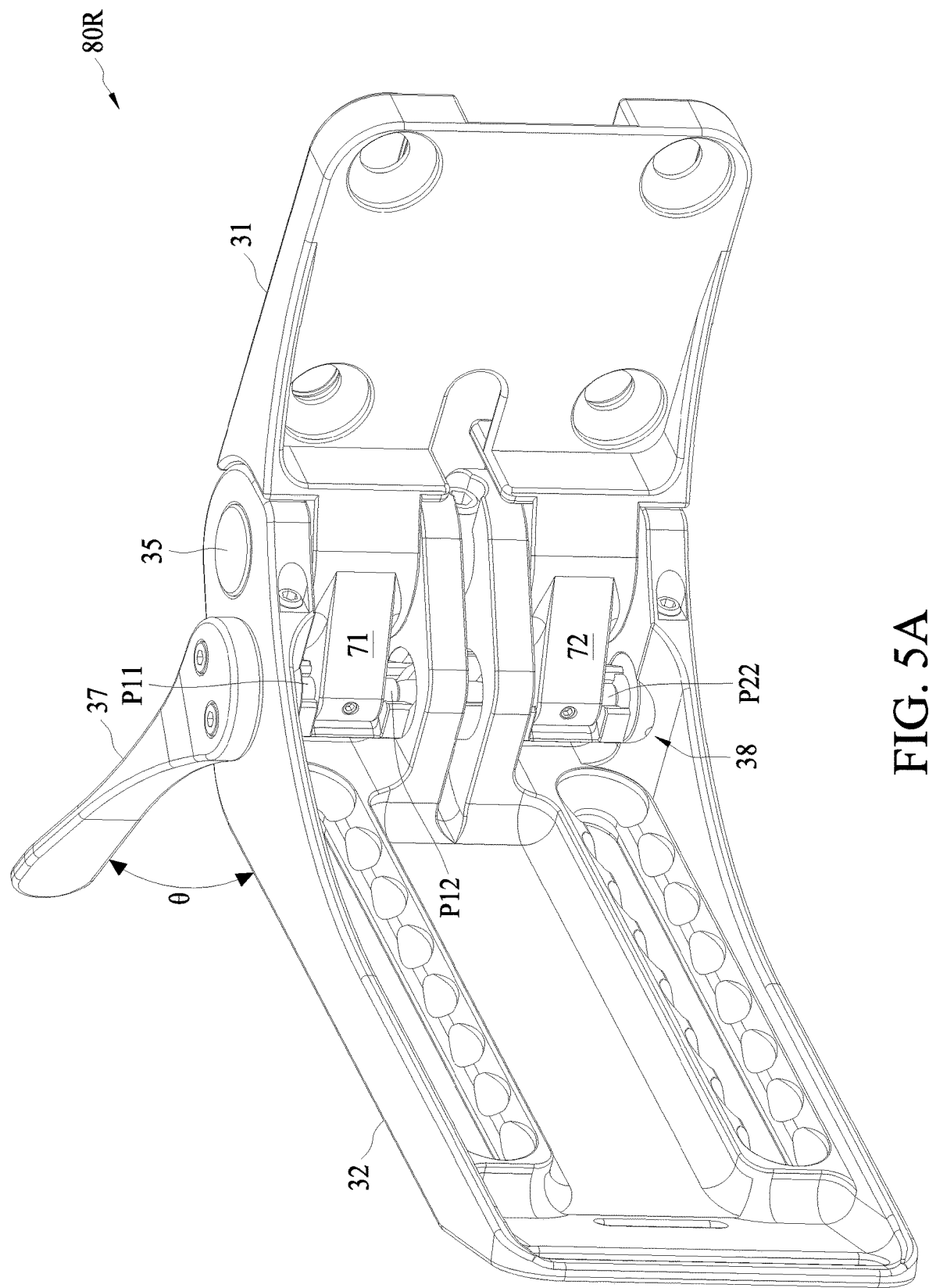
FIG. 5A is a perspective view of the right adjusting assembly illustrated in FIG. 1B in an unlocked state, in accordance with some embodiments of the present invention.

FIG. 5A is a perspective view of the right adjusting assembly 80R illustrated in FIG. 1B in an unlocked state, in accordance with some embodiments of the present invention.

Referring to FIG. 5A, when the second shaft 38 is rotated by the lever 37 to a second position, the second plate 32 is unlocked. In an embodiment, an angle θ between the first position to lock the second plate 32 and the second position to unlock the second plate 32 is approximately 135 degrees. As previously discussed, the pins P11, P12, P21 and P22 are immobile with respect to the second plate 32. In a process changing the second plate 32 from a locked state to an unlocked state, since the second shaft 38 rotates as the lever 37 rotates, the pins P11, P12, P21 and P22 are no longer held in the recesses R1, R2 and R3, and are released from the second shaft 38. As shown in FIG. 5A, these pins P11, P12, P21 and P22 are exposed from the second shaft 38.

Figure 5B:
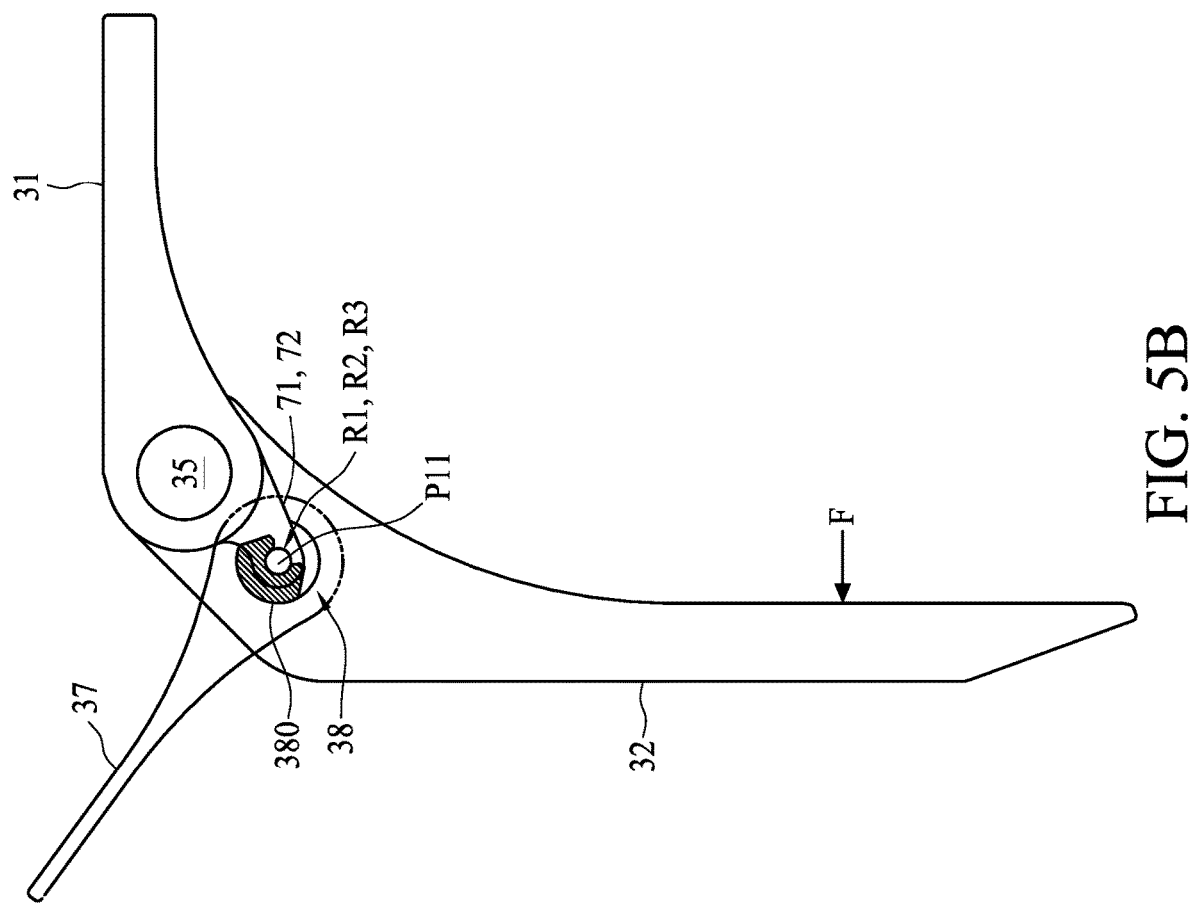
FIG. 5B is a schematic top view of the right adjusting assembly illustrated in FIG. 5A.

FIG. 5B is a schematic top view of the right adjusting assembly 80R illustrated in FIG. 5A.

Referring to FIG. 5B, the body 380 at the second position is about to disengage the first block 71 and the second block 72. Meanwhile, the pins P11, P12, P21 and P22 are about to be released from the second shaft 38. Consequently, when an external force F is applied to the second plate 32, the body 380 no longer blocks an outward rotation of the second plate 32. As a result, during the unlocked state, the right leg assembly 12R coupled to the second plate 32 is allowed to move outwardly with respect to the central line Cl so as to reach an unfolded position.

Figure 6A:
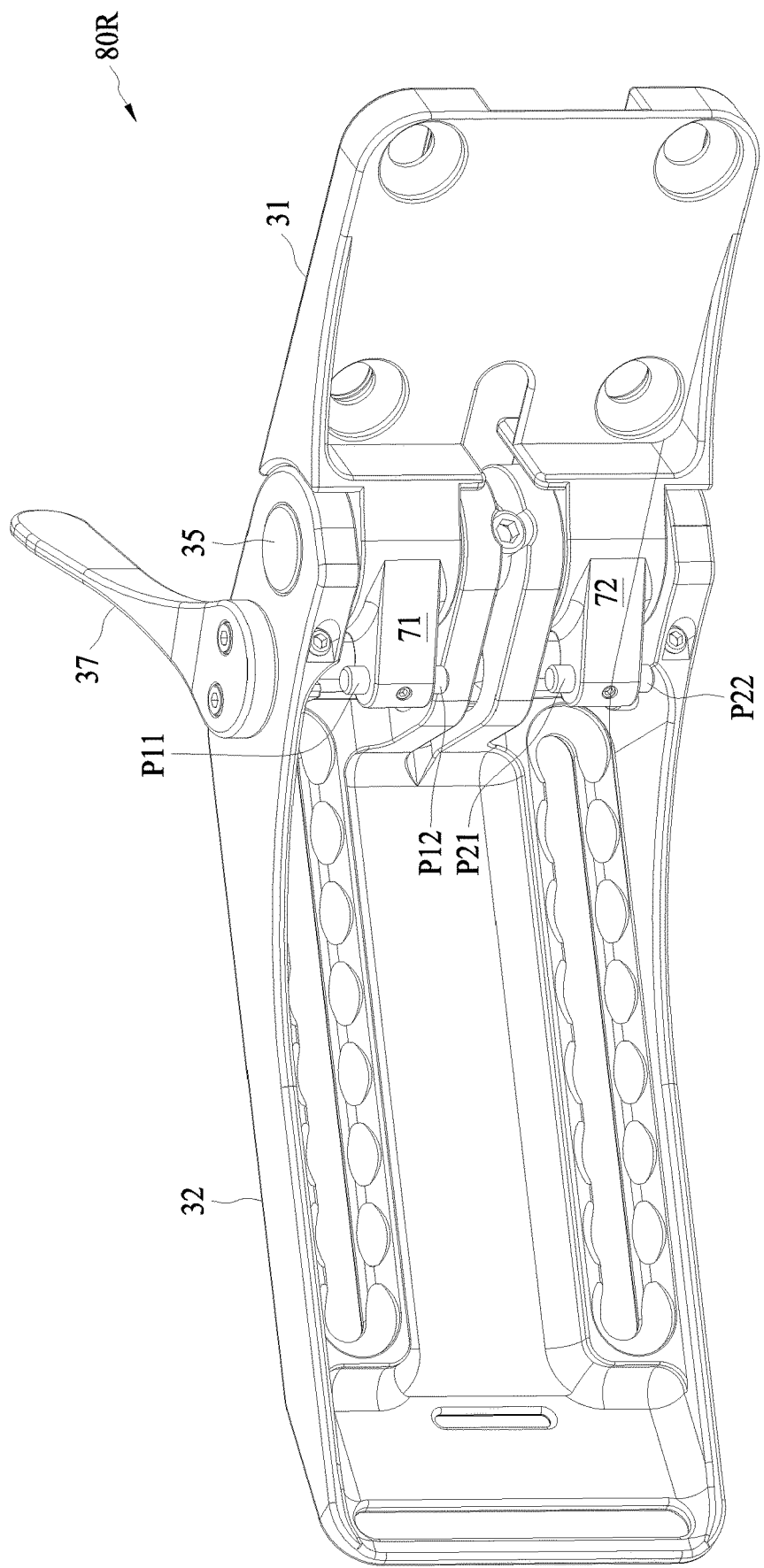
FIG. 6A is a perspective view of the right adjusting assembly illustrated in FIG. 1B with a second plate released during an unlocked state, in accordance with some embodiments of the present invention.

FIG. 6A is a perspective view of the right adjusting assembly 80R illustrated in FIG. 1B with the second plate 32 released during an unlocked state, in accordance with some embodiments of the present invention.

Referring to FIG. 6A, in response to an external force F, the second plate 32 rotates about the first shaft 35 and moves away from the central line CL, which causes an unfolded position of the right leg assembly 12R.

Figure 6B:
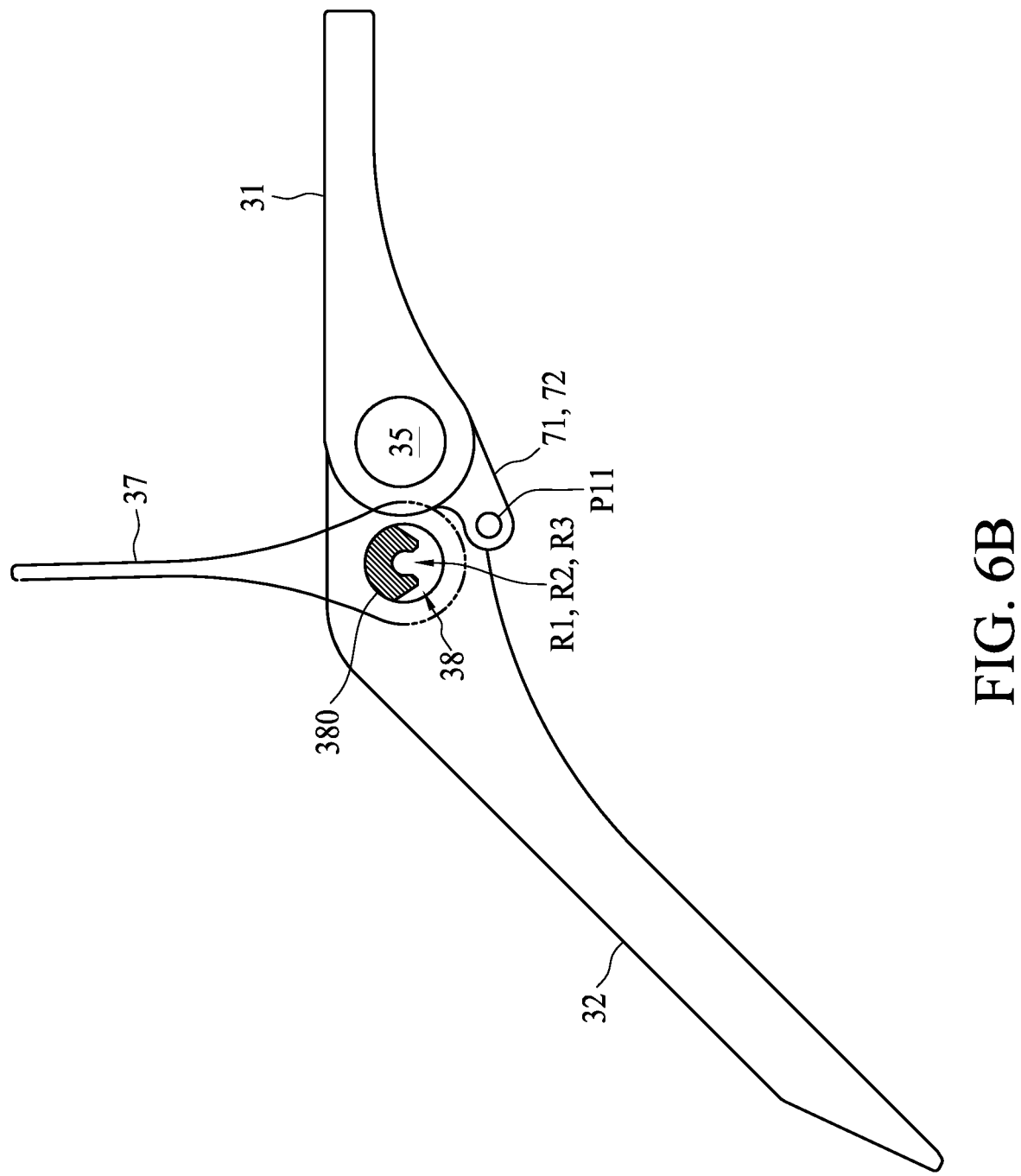
FIG. 6B is a schematic top view of the right adjusting assembly illustrated in FIG. 6A.

FIG. 6B is a schematic top view of the right adjusting assembly 80R illustrated in FIG. 6A.

Referring to FIG. 6B, the pins P11, P12, P21 and P22 as well as the first block 71 and the second block 72 are totally exposed as the second plate 32 moves away from the central line CL.

In some existing approaches, a belt is used for adjusting a leg assembly between folded and unfolded positions. The belt may become less elastic over its life span and eventually lose its elasticity, resulting in elastic fatigue or deformation. An elastically deformed belt may be liable to getting loose or inadvertently pop out during use. As compared to such approaches, the adjusting assemblies 80R and 80L according to the present invention are more robust and reliable. In addition, the adjusting assemblies 80R and 80L may also be applicable to the shank for ease of wearing an exoskeleton robot.

Although the present invention and its advantages have been described in detail, it should be understood that various changes, substitutions and alterations can be made herein without departing from the spirit and scope of the invention as defined by the appended claims. For example, many of the processes discussed above can be implemented in different methodologies and replaced by other processes, or a combination thereof.

Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed, that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. An adjusting assembly for an exoskeleton robot, the adjusting assembly comprising:
   a first plate, including at least one pin aligned in a first direction;
   a second plate pivotably connected to the first plate via a first shaft; and a second shaft extending in parallel with the first shaft in the first direction, and including a body and at least one recess, the second shaft configured to rotate to a first position to accommodate the at least one pin in the at least one recess, and to a second position to release the at least one pin from the at least one recess, wherein at the first position the second plate is blocked from rotation about the first shaft by the body, and at the second position the second plate is allowed to rotate about the first shaft.

2. The adjusting assembly according to claim 1, wherein the first plate further includes a first block, and the at least one pin includes a first pair of pins on opposite surfaces of the first block.

3. The adjusting assembly according to claim 2, wherein the first plate further includes a second block, and the at least one pin includes a second pair of pins on opposite surfaces of the second block.

4. The adjusting assembly according to claim 3, wherein the second shaft further includes a first locking member, a second locking member and a third locking member between the first locking member and the second locking member, the first locking member, second locking member and third locking member are integral with the body.

5. The adjusting assembly according to claim 4, wherein the at least one recess further includes a first recess defined by the first locking member, the first recess configured to accommodate a first pin of the first pair of pins.

6. The adjusting assembly according to claim 5, wherein the at least one recess further includes a second recess defined by the second locking member, the second recess configured to accommodate a first pin of the second pair of pins.

7. The adjusting assembly according to claim 6, wherein the third locking member includes a first tab and a second tab, and the at least one recess further includes a third recess defined between the first tab and the second tab, the first recess, the second recess and the third recess configured to communicate with each other in the first direction.

8. The adjusting assembly according to claim 7, wherein the third recess configured to accommodate a second pin of the first pair of pins and a second pin of the second pair of pins.

9. The adjusting assembly according to claim 4 further comprising a lever connected to the first locking member of the second shaft, the lever configured to cause the second shaft to rotate as the lever rotates.

10. The adjusting assembly according to claim 1, wherein the first plate is secured to a waist assembly of the exoskeleton robot, and the second plate is connected to a leg assembly of the exoskeleton robot.

11. An exoskeleton robot, comprising:
a waist assembly;
a leg assembly; and
an adjusting assembly, comprising:
  a first plate secured to the waist assembly, the first plate including at least one pin aligned with in a first direction;
  a second plate connected to the leg assembly and pivotably connected via a first shaft to the first plate; and
  a second shaft extending in parallel with the first shaft in the first direction, and including a body and at least one recess, the second shaft configured to rotate to a first position to accommodate the at least one pin in the at least one recess, and to a second position to release the at least one pin from the at least one recess,
  wherein at the first position the second plate is blocked from rotation about the first shaft by the body, and at the second position the second plate is allowed to rotate about the first shaft.

12. The exoskeleton robot according to claim 11, wherein the first plate further includes a first block, and the at least one pin includes a first pair of pins on opposite surfaces of the first block.

13. The exoskeleton robot according to claim 12, wherein the first plate further includes a second block, and the at least one pin includes a second pair of pins on opposite surfaces of the second block.

14. The exoskeleton robot according to claim 13, wherein the second shaft further includes a first locking member, a second locking member and a third locking member between the first locking member and the second locking member, the first locking member, second locking member and third locking member are integral with the body.

15. The exoskeleton robot according to claim 14, wherein the at least one recess further includes a first recess defined by the first locking member, the first recess configured to accommodate a first pin of the first pair of pins.

16. The exoskeleton robot according to claim 15, wherein the at least one recess further includes a second recess defined by the second locking member, the second recess configured to accommodate a first pin of the second pair of pins.

17. The exoskeleton robot according to claim 16, wherein the third locking member includes a first tab and a second tab, and the at least one recess further includes a third recess defined between the first tab and the second tab, the first recess, the second recess and the third recess configured to communicate with each other in the first direction.

18. The exoskeleton robot according to claim 17, wherein the third recess configured to accommodate accommodate a second pin of the first pair of pins and a second pin of the second pair of pins.

19. The exoskeleton robot according to claim 14 further comprising a lever connected to the first locking member of the second shaft, the lever configured to cause the second shaft to rotate as the lever rotates.

20. The exoskeleton robot according to claim 11, wherein the leg assembly is disposed in a folded position in response to a locked state of the second plate, and disposed in an unfolded position in response to an unlocked state of the second plate.

* * * * *